Figure 1A:
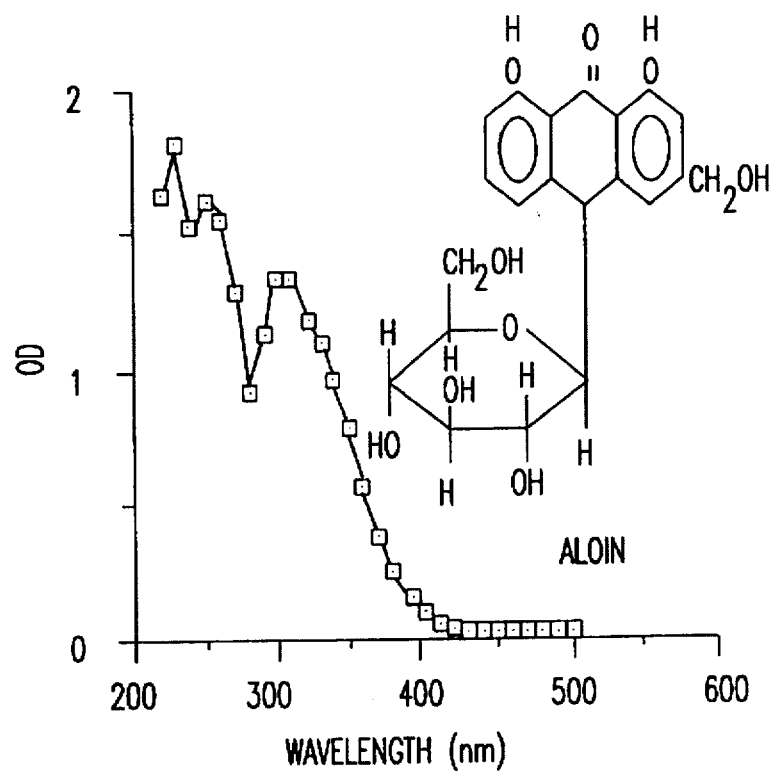
Figure 1B:
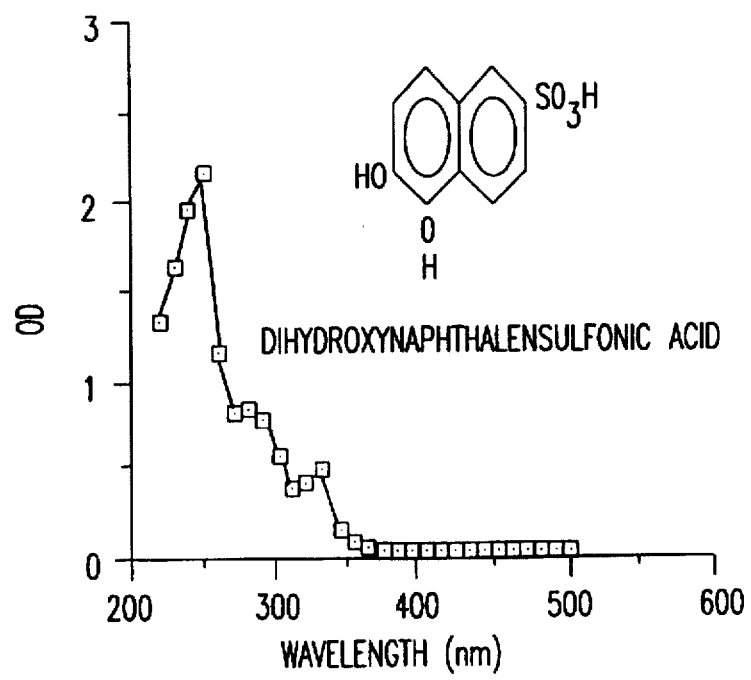
Figure 1C:
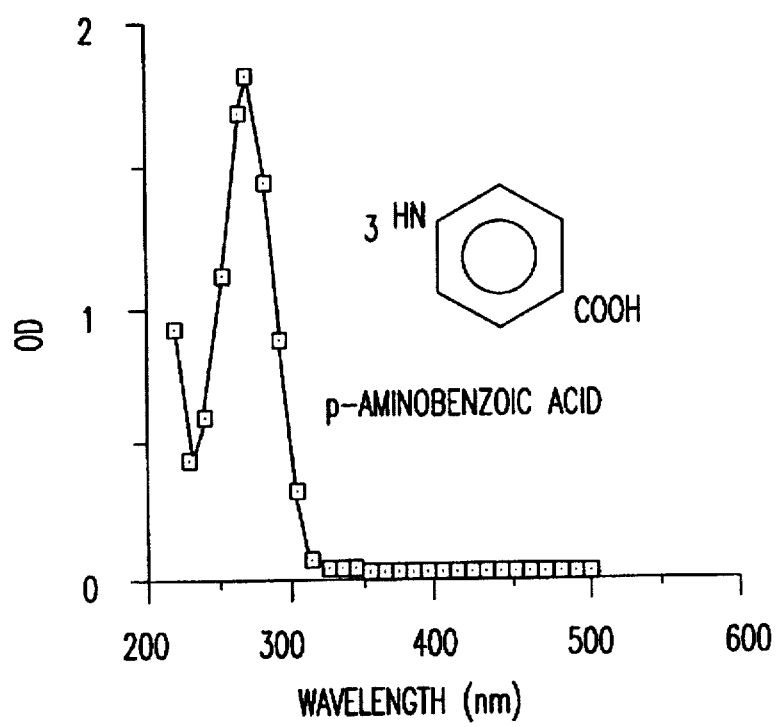
Figure 1D:
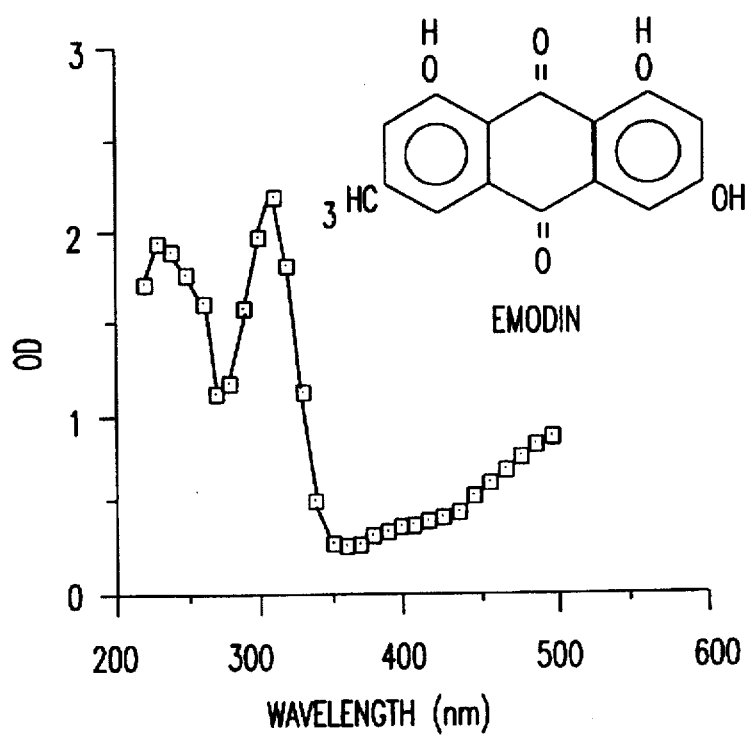
Figure 1E:
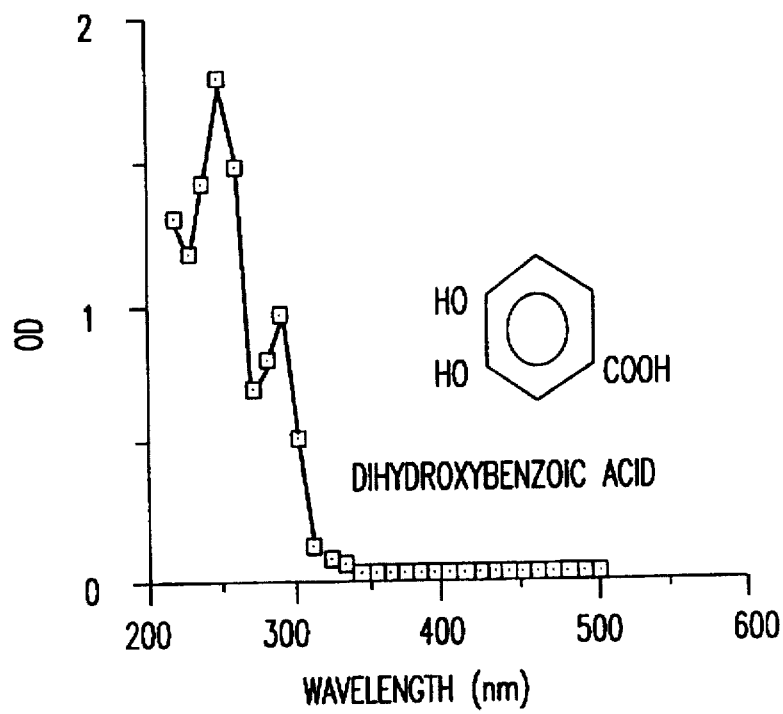
Figure 1F:
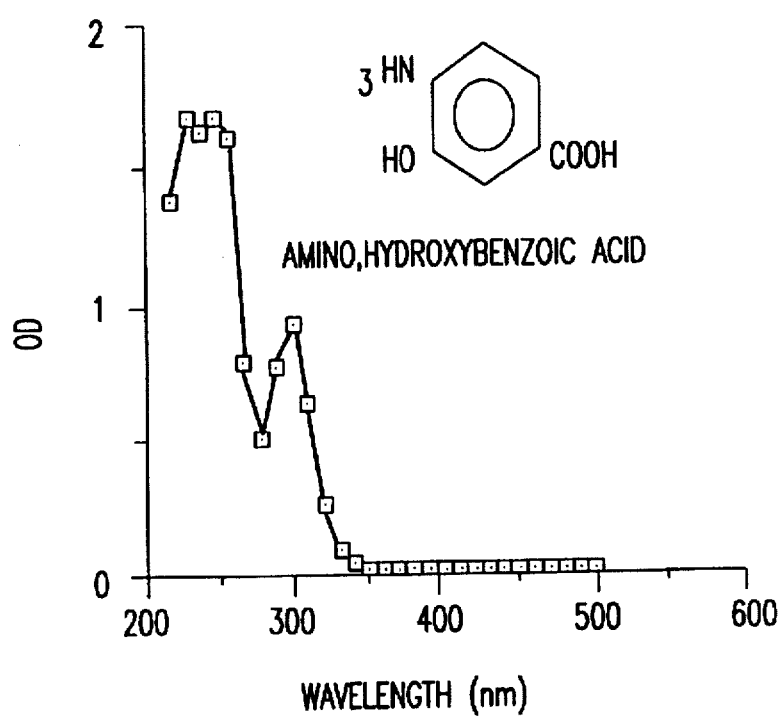
Figure 1G:
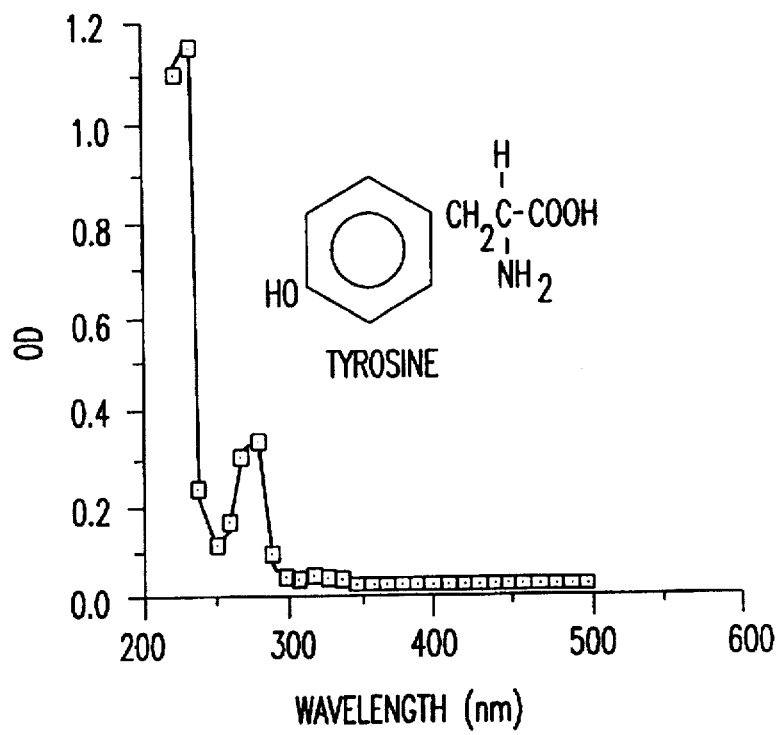
Figure 1H:
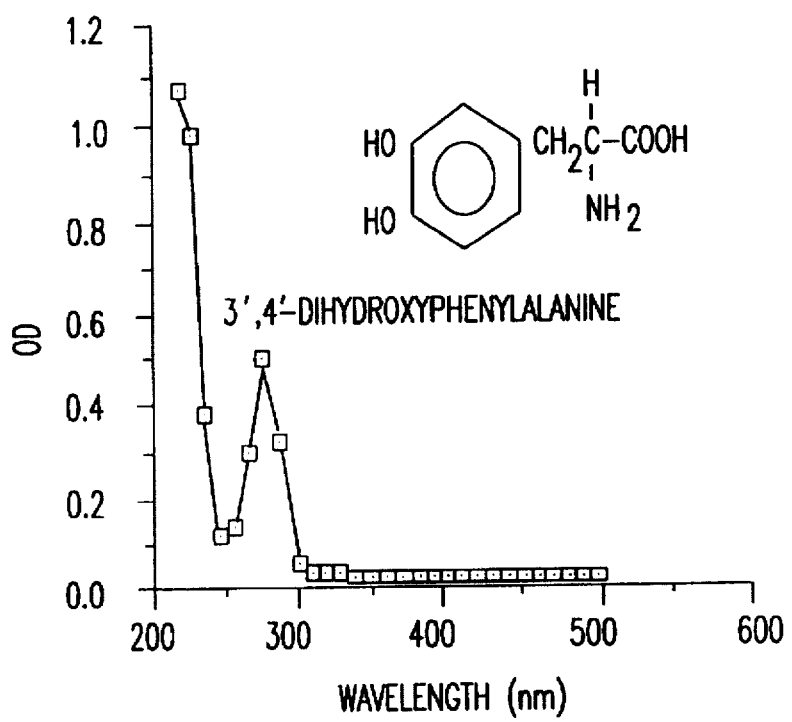
Figure 1I:
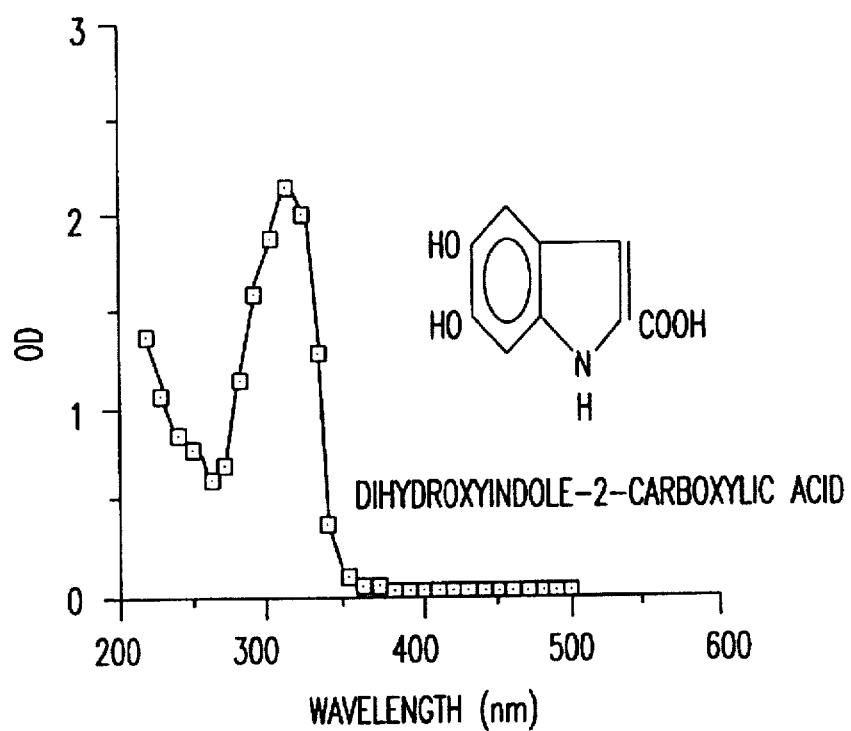
Figure 1J:
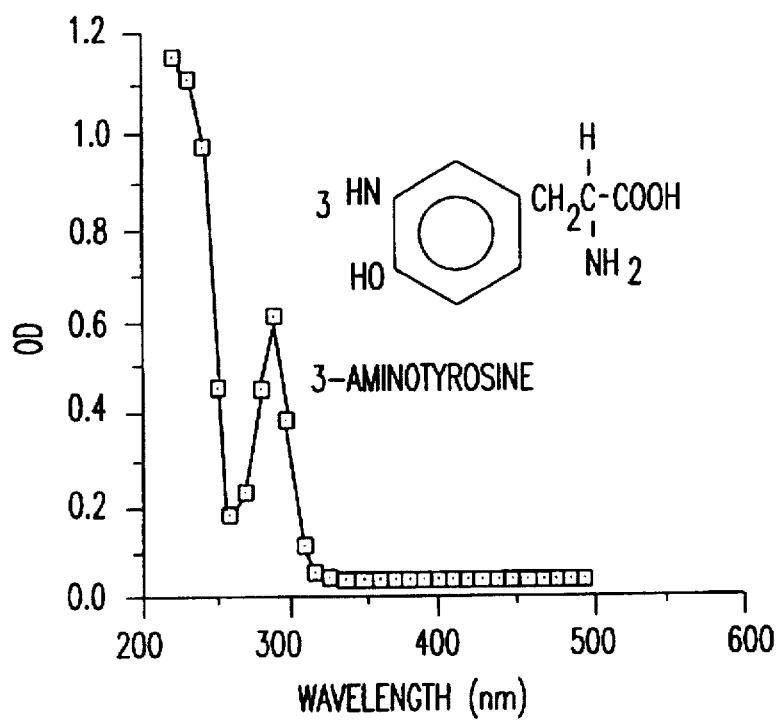
Figure 1K:
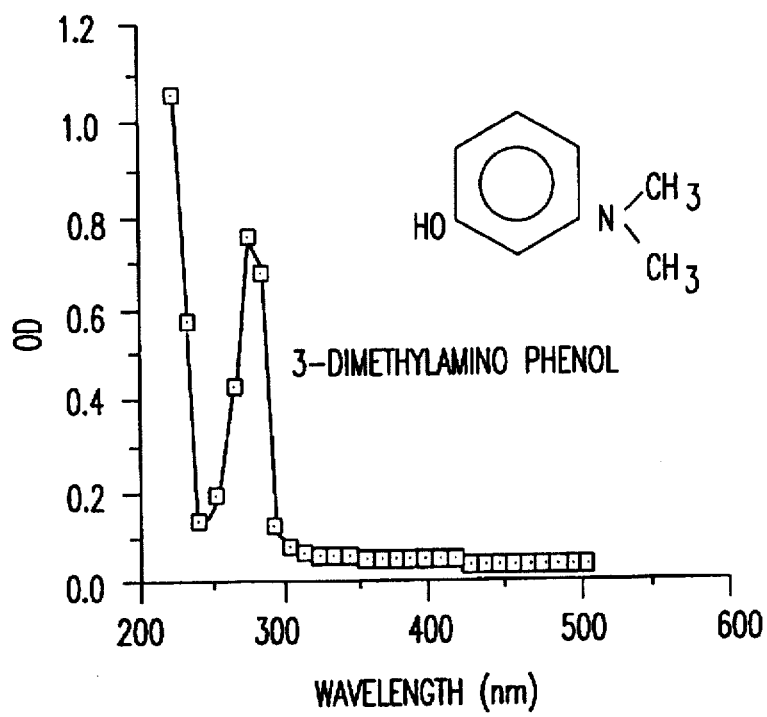
Figure 1L:
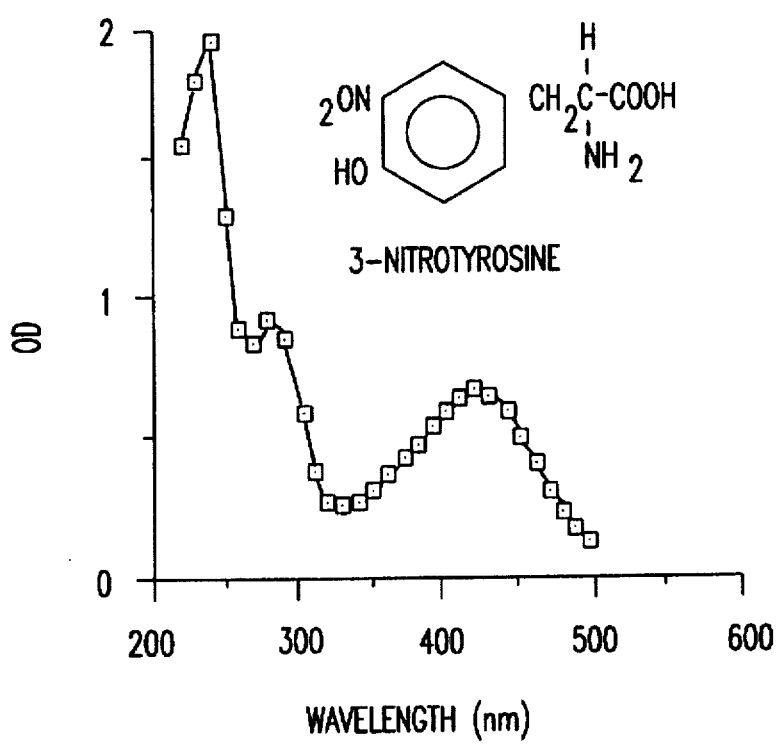

United States Patent [19]

Pawelek et al.

[11] Patent Number: 5,744,125
[45] Date of Patent: Apr. 28, 1998

[54] COSMETIC MELANINS

[75] Inventors: John M. Pawelek, Hamden; James T. Platt, Milford, both of Conn.

[73] Assignee: Yale University, New Haven, Conn.

[21] Appl. No.: 392,589

[22] Filed: Feb. 23, 1995

Related U.S. Application Data

[63] Continuation-in-part of Ser. No. 109,286, Aug. 19, 1993, abandoned.

[51] Int. Cl.$^6$ .................... A61K 7/44; A61K 7/42
[52] U.S. Cl. .................... 424/59; 424/60; 528/86; 528/171; 528/172; 528/173; 528/205; 528/206; 528/207; 528/208; 528/209; 528/210; 528/211; 528/212; 528/213; 528/214; 528/215; 528/216; 528/217; 528/218; 528/219; 528/271; 528/310; 528/311; 528/312; 528/313; 528/314; 528/315; 528/316; 528/317; 528/318; 528/319; 528/321; 528/328; 528/329.1; 528/330; 528/331; 528/363; 528/364; 528/327; 527/300; 527/303; 527/311; 527/312
[58] Field of Search .................... 424/59, 60; 528/86, 528/171, 172, 173, 205, 206, 207, 208, 209, 210, 211, 212, 213, 214, 215, 216, 217, 218, 219, 271, 310–319, 321, 328, 329.1, 330, 331, 363, 364, 327; 527/300, 303, 311, 312

[56] References Cited

U.S. PATENT DOCUMENTS

| | | | |
|---|---|---|---|
| 4,515,773 | 5/1985 | Herlihy | 514/785 |
| 4,609,544 | 9/1986 | Herlihy | 424/63 |
| 4,656,029 | 4/1987 | Grollier et al. | 424/47 |
| 4,806,344 | 2/1989 | Gaskin | 424/59 |
| 4,826,677 | 5/1989 | Mueller et al. | 424/78 |
| 4,855,144 | 8/1989 | Leong et al. | 424/487 |
| 4,961,754 | 10/1990 | Grollier | 424/69 |
| 4,968,497 | 11/1990 | Wolfram et al. | 514/937 |
| 5,006,331 | 4/1991 | Gaskin | 424/70 |
| 5,017,194 | 5/1991 | Arifoglu et al. | 8/111 |
| 5,057,325 | 10/1991 | Montefiori | 424/522 |
| 5,188,844 | 2/1993 | Ahene et al. | 424/574 |
| 5,256,403 | 10/1993 | Gaskin | 424/59 |
| 5,451,254 | 9/1995 | Andrean et al. | 106/503 |

FOREIGN PATENT DOCUMENTS

| | | |
|---|---|---|
| 2001573 | 4/1990 | Canada. |
| 598407 A2 | 5/1994 | European Pat. Off. |
| 1635139 | 1/1988 | U.S.S.R. |
| WO 92/18166 | 10/1992 | WIPO. |

OTHER PUBLICATIONS

Orlow et al., 1992, "Synthesis and Characterization of Melanins from Dihydroxyindole-2-Carboxylic Acid and Dihydroxyindole," *Pigment Cell Research* 5: 113–121.

Leonard et al., 1988, "Function of Dopachrome Oxidoreductase and Metal Ions in Dopachrome Conversion in the Eumelanin Pathway," *Biochemistry* 27:6156–6159.

Palumbo et al., 1987, "Effect of Metal Ions on the Rearrangement of Dopachrome," *Biochemical et Biophysica Acta* 925:203–209.

Pawelek et al., 1987, "The Biosynthesis of Mammalian Melanin," *American Scientist* Mar.–Apr. 70(2): 136–144.

Pawelek et al., 1992, "Molecular Cascades in UV–Induced Melanogenesis: A Central Role for Melanotropins," *Pigment Cell Research* 5:348–356.

Guiseppe Prota, "Chapter 1: An Introduction to Melanin Research and Chapter 4: Natural and Synthetic Melanins," *Melanins and Melanogenesis*, Academic Press, Inc., New York, pp. 1–13 and 63–87.

Arnow, L.E. I. (1938) "The Preparation of Dopa–Melanin", *Science* 87: 308.

Binns et al. (1970) "Studies related to the chemistry of Melanins. Part VIII. The Pyrrole–carboxylic Acids formed by oxidation of hydrolysis of melanins derived from 3,4–dihydroxyphenethylamine or (+)–3,4–dihydroxyphenylalanine", *J. Chem. Soc.* (C):1128–1134.

Debing et al. (1988) "Melanosome Binding and Oxidation–Reduction Properties of Synthetic I–Dopa–Melanin as In Vitro Tests for Drug Toxicity", *Mol Pharmacol.* 33:470–476.

Hansson et al. (1979) "Electron Spin Resonance Studies on Phaeomelanins", *Acta Dermatovener.* 59:453–472.

Montefiori et al. (1993) "Selective antiviral activity of synthetic soluble I–tyrosine and I–dopa melanins against human immunodeficiency virus in vitro," *Antiviral Research* 15:11–26.

Salazar-Bookaman et al. (1989) "Investigation by NMR spectroscopy of the interaction between synthetic soluble(−) dopa melanin and drugs", *Naunyn Schm. Arch Pharmacol* 340:576–582.

Yoshi et al. (1993) Water–soluble eumelanin as a PCR–inhibitor and a simple method for its removal, *Nippon Hoigaku Zasshi (Japan)* 58:323–329 (and English Abstract plus Applicant's partial translation).

Prota, 1976, Experientia 32:970.

*Primary Examiner*—Frederick Krass
*Attorney, Agent, or Firm*—Pennie & Edmonds

[57] ABSTRACT

Disclosed are cosmetic melanins of different colors produced by procedures involving oxidative polymerization of monomeric precursors of melanin and/or co-monomers that enhance substantivity or adherence of the melanins to the skin and hair. Also disclosed are methods for preparing cosmetic melanins and methods for using these compositions topically to produce a natural-appearing tan and to prevent damage to skin caused by UV exposure.

31 Claims, 12 Drawing Sheets

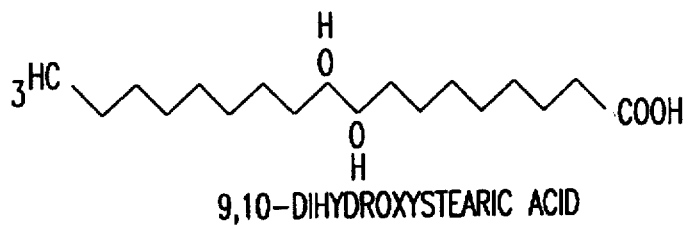
9,10-DIHYDROXYSTEARIC ACID
ALIZARIN
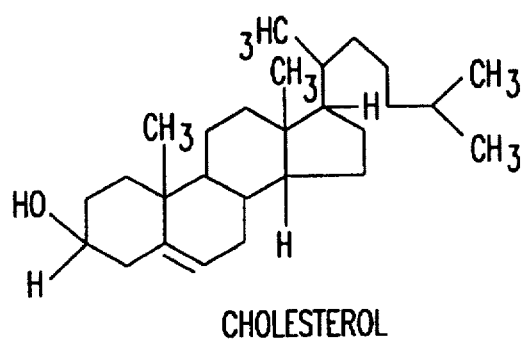
CHOLESTEROL
DIHYDROXYCARBAZOLE
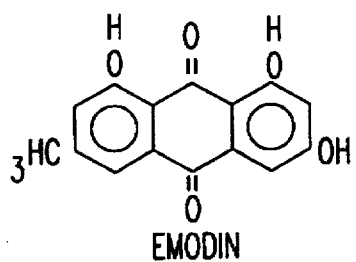
EMODIN
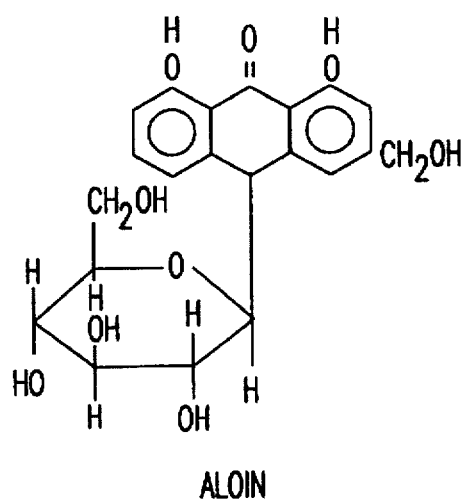
ALOIN
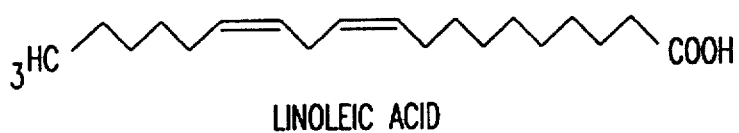
LINOLEIC ACID
FIG.3

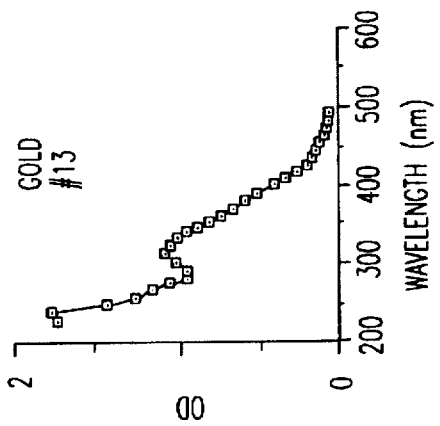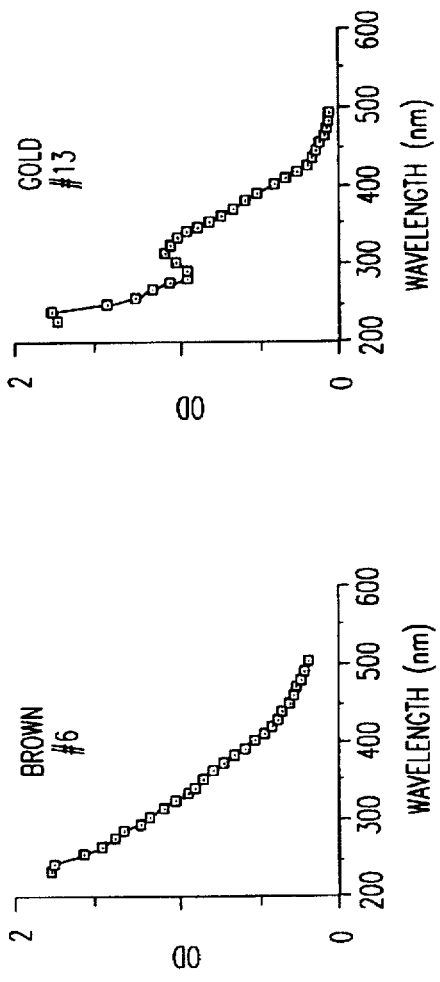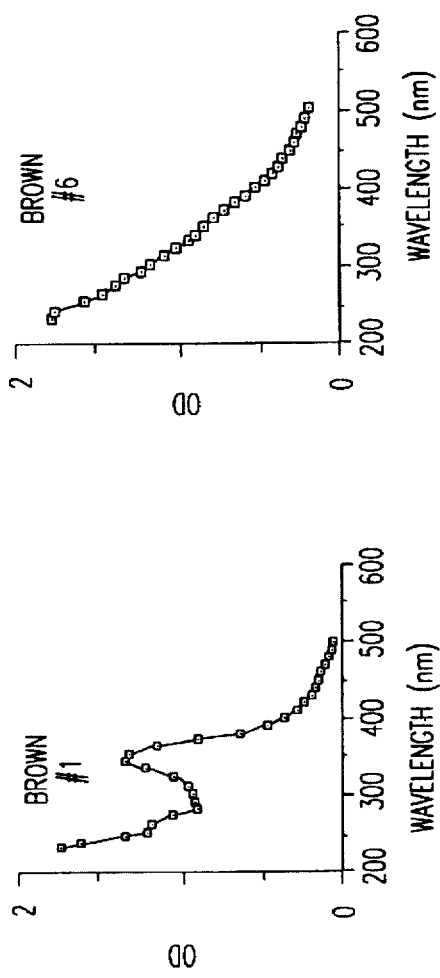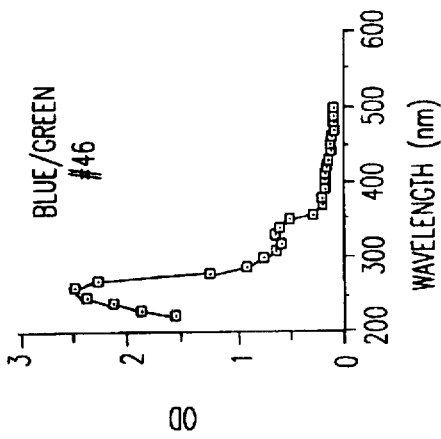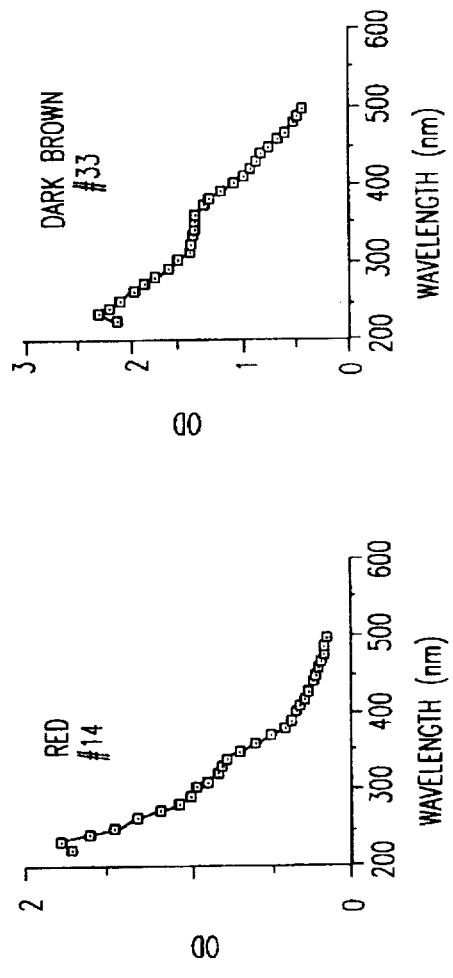

COSMETIC MELANINS

The present application is a continuation-in-part of application Ser. No. 08/109,286 filed Aug. 19, 1993, now abandoned, which is incorporated by reference herein in its entirety.

1. FIELD OF INVENTION

The present invention relates to the methods of producing soluble forms of melanin polymers and to topical compositions useful for providing a substantive, natural-appearing tan, in a variety of colors to mammalian skin and protecting the skin from the harmful effects of ultraviolet radiation.

2. BACKGROUND OF THE INVENTION

It is well established that the incidence of melanoma and other cancers of the skin is on the rise and that solar radiation, particularly that in the ultraviolet (UV) range, is a major causative factor. Pawelek et al., 1992, Molecular Cascades in UV-induced Melanogenesis: A central role for melanotropins?, *Pigment Cell Research* 5:348–356. The sensitivity of the human skin to UV exposure is determined by the amount of pigment melanin contained within the skin. In this regard, individuals with high skin melanin content are less likely to suffer from skin cancers and other damaging effects of sunlight, for example, wrinkling, solar lentigines and premature aging of the skin characterized by wrinkling and yellowing of the skin, cracking, telangiectasis (spider vessels), solar keratoses (growths), ecchymoses (subcutaneous hemorrhagic lesions), and loss of elasticity (sagging).

Public awareness of these facts has led to an increased usage of sunscreens that protect the skin from UV radiation. Sunscreens are now included in a diversity of personal care products, particularly cosmetic-type products which are worn on a daily basis. The active ingredients of most of these sunscreens do not impart a tan to the skin. However, many individuals who use sunscreens also desire to have tan-appearing skin.

There are a variety of agents available which provide a tan color to the skin, but few, if any, of these provide significant protection from UV-induced damage to the skin. For example, dihydroxyacetone (DHA) provides color through a reaction with specific amino acids in the stratum corneum. A drawback of this type of product is that it results in uneven coloration. In addition, DHA provides little, if any, protection from ill-effects of excessive UV exposure.

Related products in the field include artificial tanning compositions comprising melanin precursors or melanin precursor-like materials. These products do not contain natural or synthetic melanins. For example, some compositions achieve only superficial external tanning results which are readily removed by rinsing with water or rubbing with a towel. Wolfram et al., U.S. Pat. No. 4,948,497. Other compositions contain a melanin precursor and a tyrosinase enzyme in a cosmetic base. Herlihy, U.S. Pat. No. 4,515,773 and Gaskin, U.S. Pat. No. 4,806,344. Some pre-formed melanins, either synthetic or natural, are subjected to a variety of chemical procedures that modify the color of these melanins. Ahene and Chedekel, U.S. Pat. No. 5,188,844. However, these procedures required pre-formed melanins as starting materials.

Mammalian melanins have proven difficult to study because they are highly insoluble and require severe treatments such as boiling in strong alkali, or the use of strong oxidants such as hydrogen peroxide, which often damage the melanins. See Prota et al., 1992, in Melanins and Melanogenesis, *Academic Press Inc.* Harcourt Brace Jovanovich, 3–4. Thus, previous attempts at producing melanin compositions which are soluble at physiological pH and temperatures in cosmetic buffers, have met limited success in the past.

Synthetic soluble melanins have been produced non-enzymatically using dihydroxyindole-2-carboxylic acid (DHICA) and/or dihydroxyindole (DHI) as precursors. Pawelek et al., U.S. Pat. No. 5,218,079; and Orlow et al., 1992, *Pigment Cell Research* 5:113–121. It was further shown that polymerization of melanins could be carried out above pH 7 in the presence of oxygen, oxidative agents such as hydrogen peroxide and by salts of metals such as $Cu^{2+}$. U.S. Pat. No. 5,216,116. However, the melanins produced were limited in their range of colors and in their substantivity or ability to adhere to the skin and hair.

Other cosmetic melanins have been described in U.S. Pat. No. 5,225,435 and U.S. Pat. No. 5,216,116.

Citation and identification of any reference in Section 2 of this application shall not be construed as an admission that such reference is available as prior art to the present invention.

3. SUMMARY OF THE INVENTION

It is an object of the present invention to provide improved methods of synthesizing synthetic forms of high molecular weight melanins that are soluble in aqueous cosmetic buffers at physiologic pH and temperatures.

It is further an object of the invention to provide melanin polymers produced from precursor monomers that are aromatic compounds having an ionizable side group including 3-aminotyrosine, 5,6-dihydroxyindole, dihydroxyindole-2-carboxylic acid, 3,4-dihydroxybenzoic acid, 3-amino,4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol and p-aminobenzoic acid.

It is a still further object of the invention to provide compositions and methods for the co-polymerization of a monomer with a co-monomer to form a synthetic melanin polymer. The co-monomers enhance certain properties of the resultant melanin polymer, for example, enhanced adherence to skin, enhanced protection from ultraviolet light and color modification. The co-monomers include 9,10-dihydroxystearic acid, cholesterol, dihydroxycarbazole, aloin, emodin, alizarin, linoleic acid and linolenic acid.

The present invention also relates to methods for producing soluble cosmetic melanin polymers using six different procedures entailing oxidation of a monomer or monomer-co-monomer combination: (a) in the presence of a weak base; or (b) in the presence of a weak base and a salt of $Cu^{++}$ or $Fe^{++}$; or (c) in the presence of a weak base, a salt of $Cu^{++}$ or $Fe^{++}$ and an oxidant; or (d) in the presence of a strong base; or (e) in the presence of a strong base and a salt of $Cu^{++}$ or $Fe^{++}$ ; or (f) in the presence of a strong base, a salt of $Cu^{++}$ or $Fe^{++}$ and an oxidant, and precipitating the melanin polymer with a lower alkanol.

The present invention relates to compositions and methods for producing soluble cosmetic melanin polymers having a wide variety of natural-appearing tan colors; and increasing the adherence of such soluble melanin polymers to mammalian skin. The present invention also relates to a composition useful for topical application comprising a tan-producing effective amount of melanin polymer to the skin.

The present invention also encompasses production of soluble melanin polymers at an industrial scale.

The present invention relates to a composition useful for topical application comprising a photoprotectively effective amount of melanin polymer to the skin.

The present invention also relates to a method of inhibiting the deleterious effects of UV radiation to skin comprising applying a photoprotectively effective amount of melanin polymer to the skin.

3.1. DEFINITIONS

As used herein, "substantive" means adhering to the skin and not being washed off with water and soap after conventional topical application of the cosmetic melanin composition to skin.

As used herein, "topical application" means directly laying on or spreading on outer skin.

As used herein, "effective amount" means an amount of the melanin composition sufficient to significantly induce a positive modification in achieving a natural-appearing tan in the skin and/or protection from damage caused by UV exposure.

The present invention can be more fully understood by reference to the following detailed description and illustrative examples as well as the figures which follow.

4. BRIEF DESCRIPTION OF THE DRAWINGS

FIGS. 1(A) and (B) describe the chemical structure and spectra of representative precursor monomers used in the production of the present melanins. The precursors share the common characteristics of possessing at least one aromatic ring and at least one ionizable side group. Except for P-aminobenzoic acid, the precursors contain an hydroxyl group. Each of the precursors absorbs light in the ultraviolet spectra. Several representative precursors, i.e., aloin, emodin and alizarin (the latter of which is not shown in FIG. 1), which can be polymerized into red, gold and purple melanins respectively, are also "melanin-enhancing" agents in that, when copolymerized with another precursor or monomer, they aid in penetration and substantivity of the cosmetic melanins to the skin.

Figure 2:
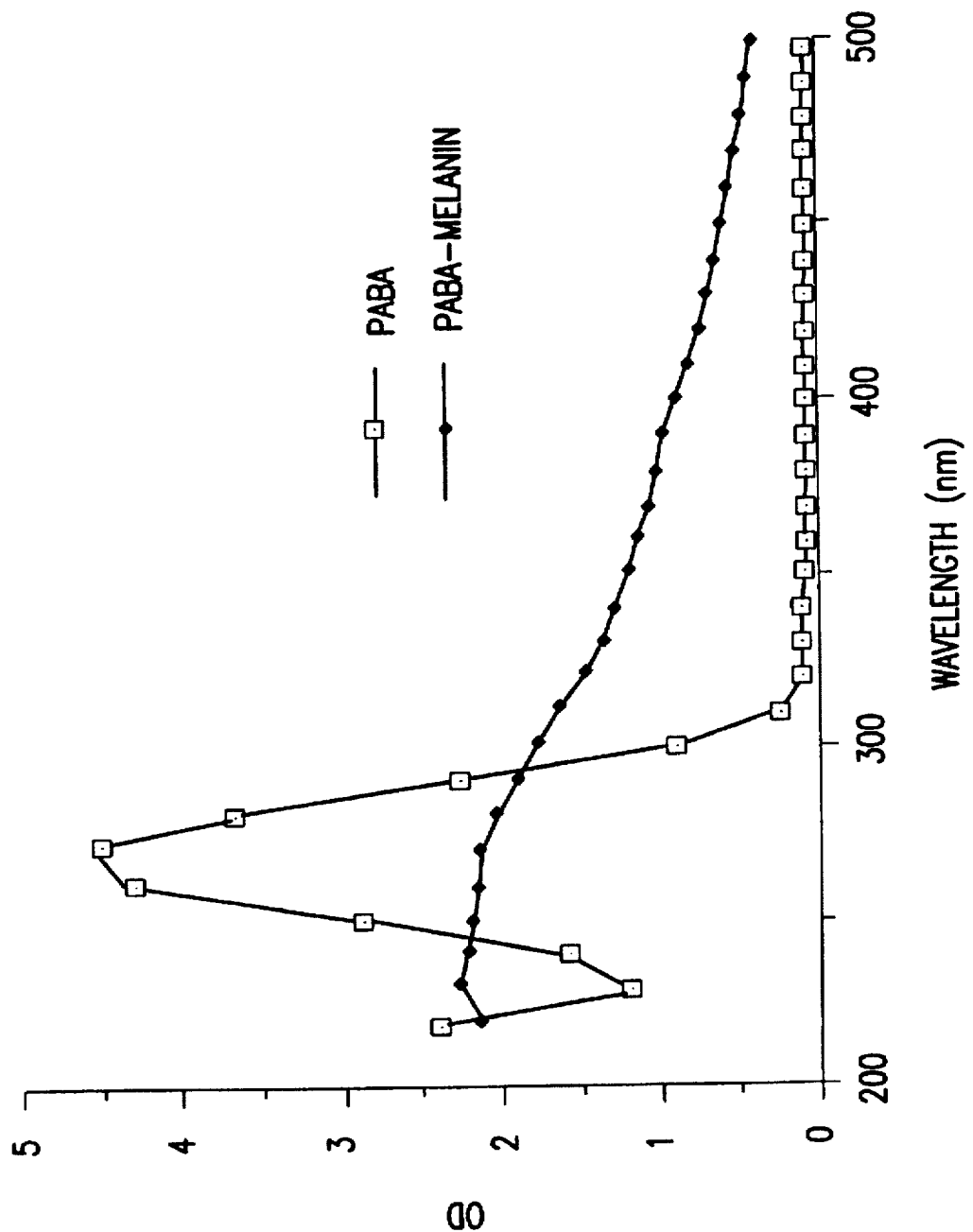
Figure 5A:
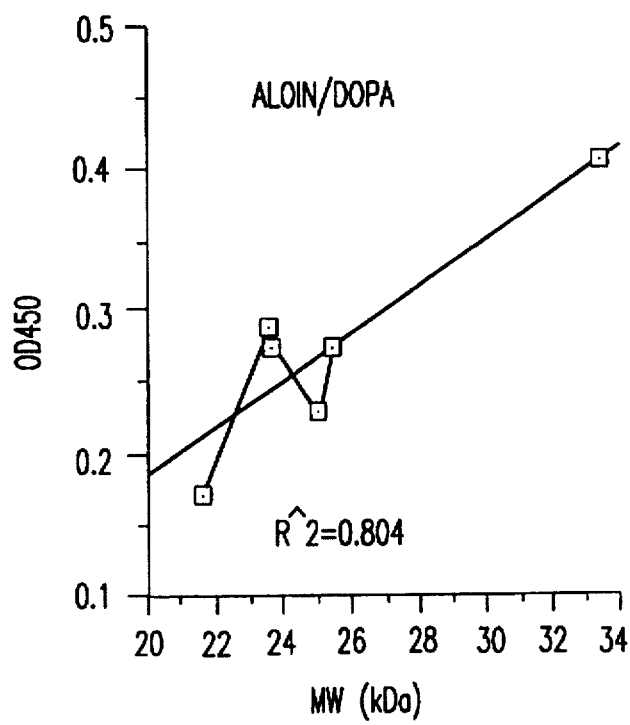
Figure 5B:
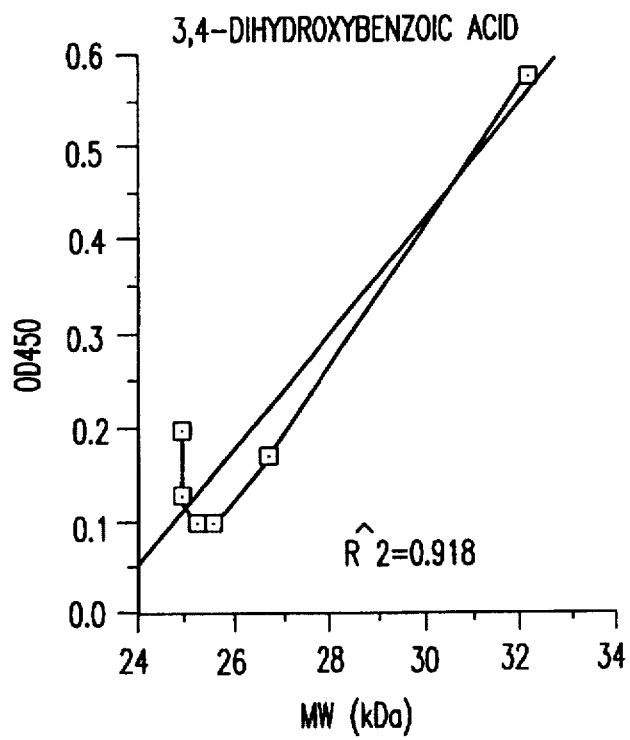
Figure 5C:
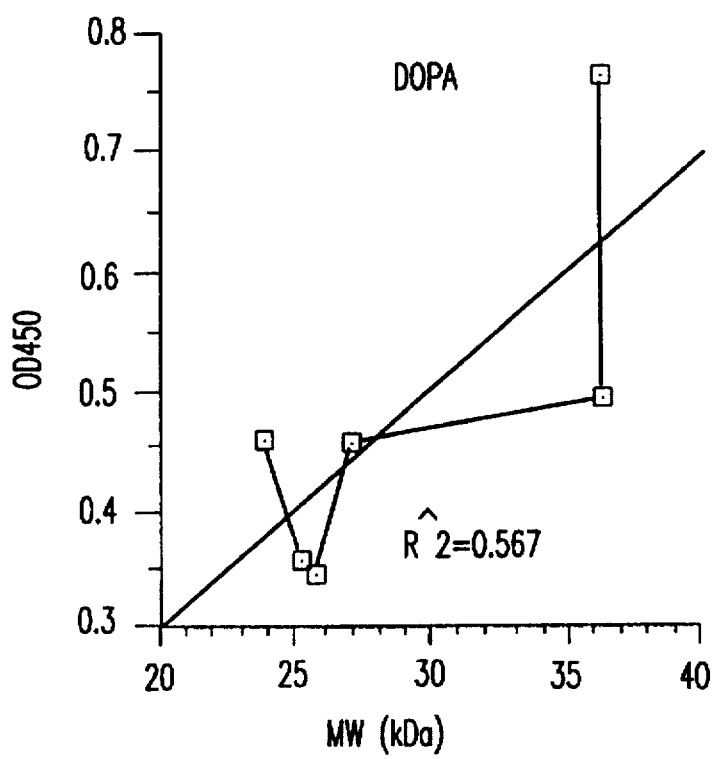
Figure 5D:
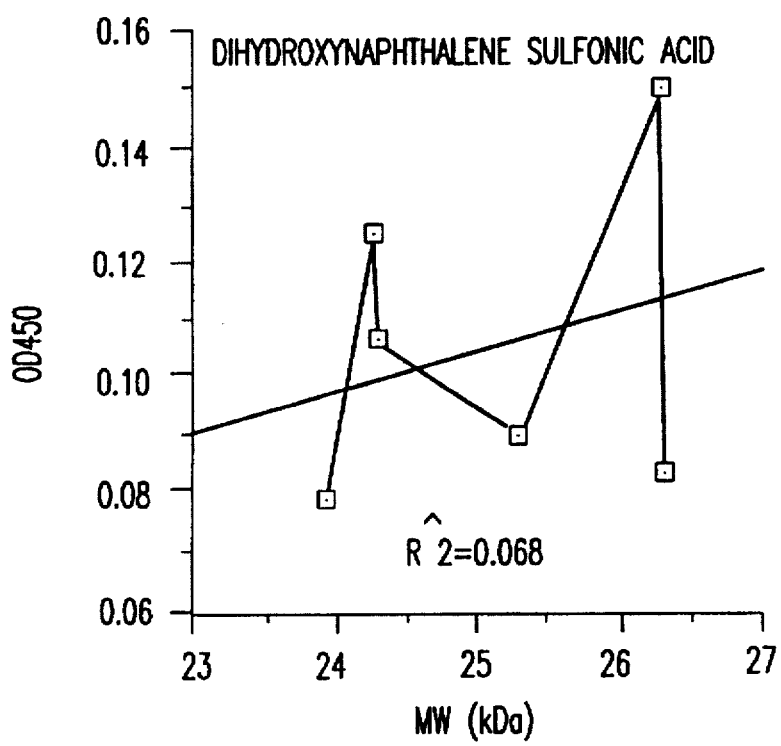
Figure 5E:
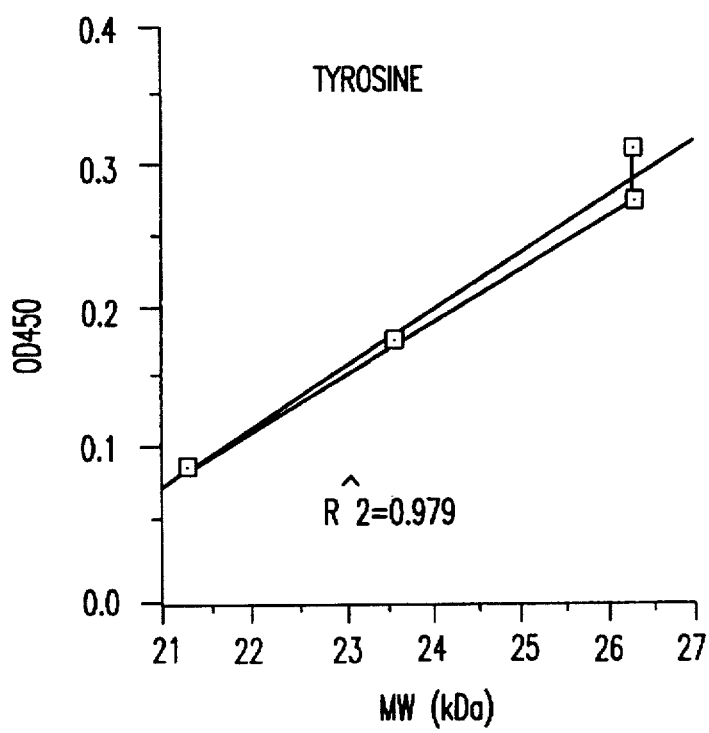
Figure 5F:
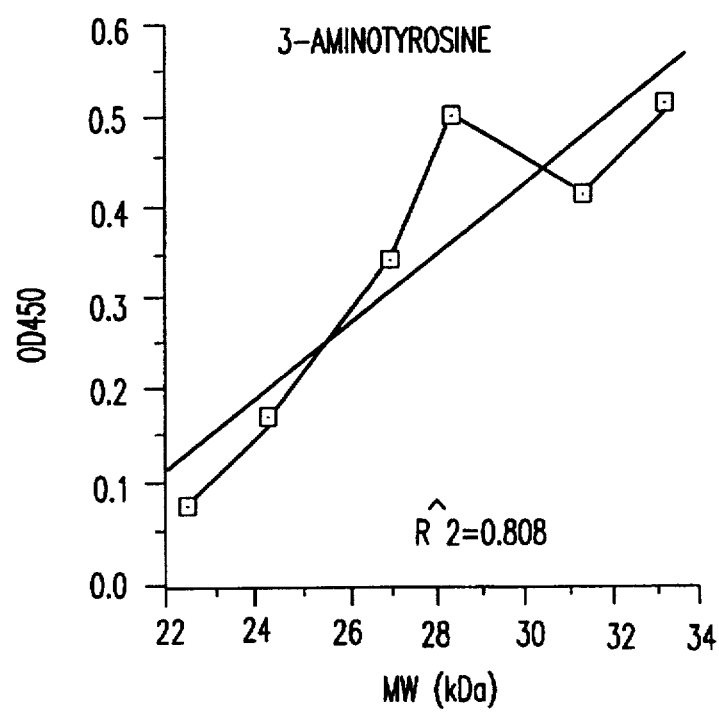

FIG. 2 describes spectral characteristics of p-aminobenzoic acid (PABA) and a synthetic, melanin-like polymer of PABA. Even though PABA does not contain an hydroxyl moiety, it could be polymerized into a high molecular weight melanin-like polymer by procedures #3 (weak base, salt of a metal ion, oxidant) and #5 (strong base, salt of metal ion) discussed infra in Section 5.3. The dried powders of PABA monomer and PABA-polymers were separately dissolved in 0.1M sodium phosphate, pH 7.4 at a concentration of 50 µg/ml, and absorbance was determined in a spectrophotometer over the range of wavelengths shown. The melanin-like PABA polymer showed a much broader absorbance range than did PABA itself, demonstrating that the polymer is a superior absorbent of light when compared to the precursor.

FIG. 3 describes the chemical structures of representative "melanin enhancing" agents used in the production of cosmetic melanins. Such agents can be copolymerized with one or more of the representative precursors in FIG. 1 to yield cosmetic melanins with enhanced penetration and substantivity to the skin when compared with melanins produced without the "melanin-enhancing" agents. The melanin enhancing agents are drawn from different chemical classes (fatty acids, steroids, alkaloids, "aloins" or "anthraquinones") but are generally both lipophilic (or possess lipophilic regions), hydroxylated, and/or exhibit unsaturated double bonds. Additional enhancing agents include extracts of Aloe Vera and related plants that are rich in aloins, emodins and alizarin.

FIG. 4 shows the spectral characteristics of representative cosmetic melanins of various colors. Melanins were synthesized with or without "melanin-enhancing" agents by one of the six procedures discussed infra in Section 5.3. Dried melanin powders were dissolved in 0.1M sodium phosphate, pH 7.4, at a concentration of 50 µg/ml and absorbance was determined in a spectrophotometer over the range of wavelengths shown. Unlike the precursors shown in FIG. 1, each of the melanins exhibited absorbance in both the ultraviolet and visible spectra.

FIG. 5 describes the relationship between molecular weights vs. absorbance (450 nm) of representative melanin polymers of the present invention. Molecular weights were calculated using the elution times from a precalibrated molecular sieve HPLC column. Absorbance of a 50 µg/ml sample was determined with a spectrophotometer. Generally, but not always, there was a correlation between the degree of absorbance and the degree of polymerization.

5. DETAILED DESCRIPTION OF THE INVENTION

The present invention provides a set of unique compositions, methods, and uses for synthetic cosmetic melanins that satisfy the following criteria:

1) Natural-appearing tan colors;
2) Adaptive to different skin/hair colorations;
3) Natural and/or organic composition;
4) High molecular weight polymers, free of monomers and reagents;
5) Ultraviolet radiation absorbent;
6) Soluble in aqueous cosmetic buffers (e.g., triethanolamine, sodium phosphate) at physiologic pH and temperature;
7) Ease of application;
8) Substantive to skin (water/soap resistant);
9) Non-spreading from skin to clothing/towels;
10) Non-mutagenic;
11) Non-irritant, non-allergenic;
12) Feasible industrial-scale production; and
13) Environmentally safe.

Although some of these criteria have been satisfied by previous "melanins", no simple component has satisfied all of these criteria, which together constitute a complete definition of "cosmetic melanin".

The present invention relates to synthetic melanin polymers that exhibit physico-chemical properties suitable for cosmetic applications--including natural-appearing tan colors, solubility in aqueous buffers at physiologic pH and temperatures, substantivity to human skin and hair, and protection from ultraviolet radiation. The present invention also relates to synthetic melanin polymers whose monomeric structures are composed of aromatic rings that possess an ionizable side group.

In addition, this invention provides a series of distinctly different methods for the oxidative polymerization of melanin precursors or monomers that yield reproducibly different melanins, even when the same precursors or monomers are used as starting material. Although it is well known that melanins can be synthesized through oxidative polymerization of appropriate precursors such as, for example, dihydroxyphenylalanine, it was not previously known until this invention that different procedures of oxidative polymerization could yield melanins with reproducibly different physical characteristics such as molecular weight and color.

Nor was it known that a wide variety of compounds from different chemical classes can be polymerized or copolymerized through such procedures and that said procedures can thus be used together to screen for new melanins, polymerized from different precursors or combinations thereof.

A key factor in the development of the above-mentioned cosmetic melanins was development of techniques for the synthesis of melanins soluble at physiological pH and temperature in cosmetic aqueous buffers.

Thus, the present invention also relates to six specific non-enzymatic methods for polymerization of monomers into synthetic melanins. These methods can also be used to screen untested, monomeric structures for their incorporation into melanin polymers, and thus for their potential suitability as precursors for the production of additional synthetic melanins.

In addition, these methods may also be used for the copolymerization of "melanin-enhancing" agents into the melanin polymer, examples being agents that improve the properties of the melanins with regard to adherence to skin, protection from ultraviolet light, and color characteristics.

The present invention also relates to methods for producing such melanins in industrial scale quantities.

The present invention relates to the topical use of compositions containing synthetic melanins to impart a tan to the skin while, at the same time, preventing the deleterious effects of UV radiation to the skin in the human population.

5.1. MONOMERIC PRECURSORS OF COSMETIC MELANINS

Generally, the precursors or monomers most amenable to polymerization have hydroxylated aromatic rings with an ionizable side group. The precursors share the common characteristic of at least one aromatic ring and at least one ionizable side group (See FIG. 1). However, even though p-aminobenzoic acid (PABA) is not hydroxylated, it can be polymerized into melanin by two of the six procedures described below in Section 5.3. PABA is widely used as a sunscreen and PABA-melanin according to the present invention, absorbs over a broader range of the UV spectrum than does PABA alone (FIG. 2).

Other suitable precursors of melanin include 3-aminotyrosine, 5,6-dihydroxyindole, dihydroxyindole-2-carboxylic acid, 3,4-dihydroxybenzoic acid, 3-amino,4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol and p-aminobenzoic acid.

5.2. CO-MONOMER COMPOUNDS USED IN SYNTHESIS OF COSMETIC MELANINS

Co-monomer compounds can be copolymerized along with the precursors monomers, yielding melanins that are uniquely applicable to cosmetic usage. Representative examples of such molecules are fatty acids such as linoleic acid, 9,10-dihydroxystearic acid, and linolenic acid; steroids such as cholesterol; and carbazole alkaloids such as dihydroxycarbazole. Examples of additional co-monomers or enhancing agents that can be included in the polymerization reactions include aromatic glycosides such as those found in extracts of the Aloe Vera plant, and related plants. The melanin-enhancing agents "aloin", "emodin" and "alizarin" are known to be ingredients of Aloe Vera and related plants. In addition, aloin, emodin and alizarin can function both as melanin precursors or monomers and as melanin enhancers, in that when polymerized alone by the procedures of the invention they yield melanin polymers with gold, red and purple colors, respectively. (See FIGS. 3–5). When they are copolymerized with other precursors, e.g., dihydroxyphenylalanine (dopa), they enhance the penetration and substantivity of the dopa-melanin polymer to the skin.

5.3. METHODS OF PREPARING COSMETIC MELANINS

5.3.1. METHODS FOR POLYMERIZATION OF MONOMERS

The melanin polymers of the present invention are produced by any one of six different procedures which involve oxidation of a monomer in the presence of air (or oxygen) under specific conditions. For example, a monomeric precursor (10% wt/vol) in water or aqueous solution, is subjected to oxidative polymerization as follows:

Procedure 1: In the presence of a weak base such as ammonium hydroxide (from about 5M to about 10M) or triethanolamine (from about 5M to about 10M);

Procedure 2: In the presence of a weak base such as ammonium hydroxide (from about 5M to about 10M) or triethanolamine (from about 5M to about 10M) and a salt of a metal ion such as $Cu^{++}$ or $Fe^{++}$;

Procedure 3: In the presence of a weak base such as ammonium hydroxide (from about 5M to about 10M) or triethanolamine (from about 5M to about 10M), a salt of a metal ion such as $Cu^{++}$ or $Fe^{++}$, and an oxidant such as hydrogen peroxide (about 3% vol/vol) or ammonium persulfate (about 30% wt/vol);

Procedure 4: In the presence of a strong base such as sodium hydroxide (from about 0.1M to about 4M) or potassium hydroxide (from about 0.1M to about 4M);

Procedure 5: In the presence of a strong base such as sodium hydroxide (from about 0.1M to about 4M) or potassium hydroxide (from about 0.1M to about 4M) and a salt of a metal ion such as $Cu^{++}$ or $Fe^{++}$;

Procedure 6: In the presence of a strong base such as sodium hydroxide (from about 0.1M to about 4M) or potassium hydroxide (from about 0.1M to about 4M), a salt of a metal ion such as $Cu^{++}$ or $Fe^{++}$ and an oxidant such as hydrogen peroxide (about 3% vol/vol) or ammonium persulfate (about 30% wt/vol).

The resultant melanin polymer is precipitated by addition of a lower alcohol, for example, methanol, isopropanol and preferably ethanol (about 2.0 volumes). Alternatively, acetone can be used to precipitate the melanin polymer. The precipitate is dried in air.

5.3.2. METHODS FOR CO-POLYMERIZATION OF CO-MONOMERS WITH MONOMERS

A monomer (about 6.7% wt/vol) in water or aqueous solution is mixed with a co-monomer (about 3.3% wt/vol) and subjected to oxidative polymerization according to the six different procedures described above in Section 5.3.1.

The resultant melanin polymer is precipitated by addition of a lower alkanol, for example, methanol, isopropanol and preferably ethanol (about 2.0 volumes). Acetone also precipitates the melanin polymer. The precipitate is dried in air.

5.3.3. INDUSTRIAL PRODUCTION OF COSMETIC MELANINS

The procedures for oxidative polymerization of suitable recursors into melanins or melanin-like compounds are readily amenable to industrial-scale production of the material. A straightforward and simple synthetic route comprises a) using a monomeric precursor, optionally with a co-monomer enhancer; b) subjecting the monomer and/or co-monomer to oxidative polymerization; c) concentrating the melanin polymer into powder; and d) formulating the cosmetic melanin composition using a suitable cosmetic vehicle or buffer.

The procedures involve, but are not limited to, mixing one or more precursors (e.g., see FIG. 1) with one or more co-monomer enhancers (e.g., see FIG. 3), and subjecting the mixture to oxidative polymerization via one of the six procedures listed in Section 5.3. The resultant polymer is concentrated via precipitation by titration with an acid (e.g., HCl) or an alcohol (e.g., ethanol), or by lyophilization or drying in air. The polymer is dried to a powder, and the powder is mixed at the desired concentration (e.g., 1% wt/wt) in a suitable aqueous cosmetic buffer (e.g., triethanolamine or sodium phosphate) or in a suitable aqueous cosmetic vehicle (e.g., Avon Body Lotion).

The Avon Body Lotion contains the following ingredients:

Purified Water
Octyl Palmitate
Petrolatum
Apricot Kernel Oil
Isopropyl Palmitate
Cetearyl Alcohol
Rice Starch
Retinyl Palmitate
Tocopherol
Cholecalciferol
Glyceryl Sterate
PEG-40 Hydrogenated Castor Oil
Sodium Cetearyl Sulfate
Imidazolidinyl Urea
Triethanolamine
Methylparaben
Carbomer-941
Dimethicone
Trimethylsiloxysilicate
Disodium EDTA
Corn Oil The cosmetic melanins so produced are believed to provide protection to the skin from damage caused by UV radiation (skin cancers, wrinkling, solar lentigines, and premature aging of the skin) by virtue of the fact that the melanins strongly absorb UV light (FIGS. 2 and 4). As mentioned above, PABA is used extensively by the industry as an active ingredient in sunscreen preparations, and it can be seen in FIG. 2 that melanins synthesized from PABA absorb UV light over a broader range than does PABA itself. In this regard, melanins prepared from precursors other than PABA have similar absorbance characteristics to PABA-melanin (see FIGS. 2 and 4), and it can thus be concluded that since such melanins are both substantive to the skin and visible to the eye, they represent a significant and unique advantage over existing sunscreen formulations.

5.4. TOPICAL COMPOSITIONS AND METHODS OF USE

The cosmetic melanins of the present invention may be incorporated into a wide variety of product types. These include, for example, lotions, creams, beach oils, gels, sprays, ointments, sticks, pastes, mousses and cosmetics such as "make-up". These product types may comprise either of two basic types of carrier systems, i.e., solutions and emulsions. The term "carrier" encompasses cosmetically-acceptable non-irritating compatible components which are suitable for delivering the melanins to the skin. These carriers must of course, be sufficiently pure to render them suitable for chronic topical application to the mammalian skin.

Compositions containing the cosmetic melanins of the present invention formulated as solutions typically include a cosmetically-acceptable solvent which, in addition to being capable of having dissolved therein the cosmetic melanin at physiological pH and temperature, also possesses acceptable safety (e.g., irritation and sensitization characteristics), as well as good aesthetic properties (e.g., does not feel greasy). The most typical example of such a solvent is water. Alternatively, the solvent can be an aqueous solution. Examples of other solvents include cosmetic buffers which include: triethanolamine and sodium phosphate. An example of aqueous cosmetic buffers or vehicles preferred in the formulation of cosmetic melanin compositions is Avon Body Lotion, described above in Section 5.3.3. The aqueous cosmetic buffers contain from about 0.1% to 5.0%, of a suitable cosmetic melanin or a combination of cosmetic melanins and from 95% to about 99.9% of an acceptable aqueous cosmetic buffer or vehicle.

Emulsion carrier systems may include single emulsion melanin preparations (such as lotions and creams of the oil-in-water type and water-in-oil type) or the triple emulsion carrier systems (such as oil-in-water-in-silicone fluid emulsion type). These are well known in the cosmetic art and are useful in the present invention.

In accordance with another aspect of the invention one part by weight of any of the melanins of the invention can be blended with about 1 to 10 and preferably about 1 to 5 and especially about 3 part by weight of urea, the urea enhancing penetration of the melanin into the epidermis.

Any of the melanins of the invention can be mixed with one another to achieve a predetermined hue customized to a particular individual's skin and hair colors.

The novel melanins can be stored as dry powders and dissolved when ready for use, or can be stored as solutions. In a preferred embodiment, melanins are incorporated into liposomes in conventional manner and such liposomes used when required.

The present invention relates to methods for achieving a natural-appearing tan and protecting the skin from the harmful effects of ultraviolet exposure. Such methods comprise topical application of an effective amount of cosmetic melanins. The amount of cosmetic melanins and frequency of application will vary depending upon the level of tanning already in existence in the subject, the intensity of the sun exposure, and the level of tanning desired. An effective amount of cosmetic melanin is applied manually to the skin and/or hair of an individual desiring a natural-appearing tan. Excess material is removed by washing with soap and water. The melanin is substantive to the skin, i.e., it adheres to the skin.

6. EXAMPLES

The following examples further describe and demonstrate various embodiments within the scope of the present invention. The examples are solely for the purpose of illustration, and are not to be construed as limitations of the present invention since many variations thereof are possible without departing from its spirit and scope.

In the following illustrative examples all parts are expressed by weight unless otherwise expressed.

6.1. EXAMPLE 1: PREPARATION OF MELANINS

Melanin polymers were produced using a variety of different procedures and melanin precursors. The molecular weights of melanin polymers produced using Procedures 1–6 and different melanin monomeric precursors are shown in Table 1.

TABLE 1

Molecular Weights (K daltons) of Melanin Polymers Synthesized Using Procedures 1-6

| Precursors[b] | Procedures[a]: 1 | 2 | 3 | 4 | 5 | 6 |
|---|---|---|---|---|---|---|
| A | NA | NA | 26.3 | 21.2 | 26.3 | 23.6 |
| B | 27.0 | 23.9 | 36.2 | 25.6 | 36.2 | 25.3 |
| C | 34.3 | 31.7 | ppt | ppt | 41.4 | 28.5 |
| D | 24.3 | 22.4 | 33.4 | 28.5 | 31.7 | 27.0 |
| E | 25.3 | 25.6 | 24.9 | 26.6 | 32.1 | 24.9 |
| F | 21.8 | 21.2 | 23.0 | 23.3 | 23.6 | 23.3 |
| G | 23.9 | 25.3 | 24.3 | 24.3 | 26.3 | 26.3 |
| H | NA | NA | 22.4 | NA | 23.6 | NA |
| I | 19.1 | 22.7 | 20.4 | 22.4 | 24.9 | 23.6 |
| J | 25.3 | 24.6 | 24.9 | 24.6 | 33.4 | 21.5 |
| K | ND | ND | 14.0 | ND | ND | ND |
| L | ND | ND | ND | ND | ND | ND |

NA: negligible product
ND: Not done
ppt: poorly soluble in aqueous buffer, pH 7.4
a. Procedures:
1) weak base
2) weak base + salt of metal ion
3) weak base + salt of metal ion + oxidant
4) strong base
5) strong base + salt of metal ion
6) strong base + salt of metal ion + oxidant
b. Precursors:
A) tyrosine
B) dihydroxyphenylalanine
C) dihydroxyindole-2-carboxylic acid
D) 3-aminotyrosine
E) 3,4-dihydroxybenzoic acid
F) 3-amino,4-hydroxybenzoic acid
G) 4,5-dihydroxynaphthalene-2-sulfonic acid
H) p-aminobenzoic acid
I) aloin
J) aloin + dihydroxyphenylalanine
K) alizarin (3 parts) + dihydroxyphenylalanine (1 part)
L) alizarin

TABLE 2

Spectrophotometric Absorbance (450 nm) of Melanin Polymers (50 μg/ml) Synthesized Via Various Procedures

| Precursors[b] | Procedures[a]: 1 | 2 | 3 | 4 | 5 | 6 |
|---|---|---|---|---|---|---|
| A | NA | NA | .275 | .084 | .308 | .170 |
| B | .456 | .461 | .763 | .350 | .496 | .358 |
| C | .450 | .293 | ppt | ppt | .457 | .457 |
| D | .167 | .074 | .507 | .500 | .411 | .343 |
| E | .101 | .100 | .194 | .171 | .577 | .128 |
| F | .145 | .291 | .733 | .757 | .930 | .445 |
| G | .078 | .089 | .125 | .106 | .150 | .082 |
| H | NA | NA | .493 | NA | .584 | NA |
| I | .158 | .210 | .312 | .280 | .326 | .221 |
| J | .261 | .223 | .302 | .373 | .217 | .191 |
| K | ND | ND | .388 | ND | ND | ND |
| L | ND | ND | ND | ND | ND | ND |

NA: negligible product
ND: not done
ppt: poorly soluble in aqueous buffer, pH 7.4
a. Procedures:
1) weak base
2) weak base + salt of metal ion
3) weak base + salt of metal ion + oxidant
4) strong base
5) strong base + salt of metal ion
6) strong base + salt of metal ion + oxidant
b. Precursors:
A) tyrosine
B) dihydroxyphenylalanine
C) dihydroxyindole-2-carboxylic acid
D) 3-aminotyrosine
E) 3,4-dihydroxybenzoic acid
F) 3-amino,4-hydroxybenzoic acid
G) 4,5-dihydroxynaphthalene-2-sulfonic acid
H) p-aminobenzoic acid
I) aloin
J) aloin + dihydroxyphenylalanine
K) alizarin (3 parts) + dihydroxyphenylalanine (1 part)
L) alizarin The molecular weights of each of the precursors and/or enhancing agents are all less than 1 kilodalton, whereas the molecular weights of the polymerized melanins average between 10–40 kilodaltons or higher. It can be seen from Table 1 that the same precursor can be polymerized into melanin polymers of different molecular weights, depending on which of the six polymerization procedures is used. Molecular weights of individual melanins were calculated via their elution times from a precalibrated molecular sieve column. These results underscore the unique usefulness of the six procedures in screening new precursors for their value as monomers in cosmetic melanin polymers.

Likewise, the degree of absorbance in the visible spectrum per unit weight of melanin also differs according to the procedure and precursors employed in the polymerization reactions. In these runs, spectrophotometric absorbance at a wavelength of 450 nm was used as a criterion of absorbance in the visible range. Absorbance of each individual melanin was measured by spectrophotometric absorbance of a solution of melanin dissolved at 50 μg/ml of sodium phosphate, 0.1M, pH 7.4. It can be seen that even with a single precursor, the absorbance of the resultant melanin polymers vary according to the procedure used. The results underscore the unique usefulness of the six procedures in screening new precursors for their value as monomers and/or co-monomers in cosmetic melanin polymers (see Table 1).

In general, there was a correlation between the degree of absorbance (at 450 nm) and the degree of polymerization (molecular weight in kilodaltons). Examples of this are presented in FIG. 4 wherein plots of absorbance vs. molecular weights of various precursors are shown for melanins of different colors. In these examples, there is a correlation between absorbance and molecular weight of the polymer with each of the precursors except dihydroxynaphthalene sulfonic acid, whose absorbance characteristics show no correlation with the degree of polymerization. However, the degree of polymerization is generally proportional to the intensity of absorbance.

6.2. EXAMPLE 2: PREPARATION OF RED, BROWN AND YELLOW COSMETIC MELANINS

Aloin (10.0% wt/vol of water) was subjected to oxidative polymerization via each of six different procedures as follows: 1) in the presence of $NH_4OH$(5M); 2) in the presence of $NH_4OH$(5M) and $CuSO_4$ (0.6 mg/ml); 3) in the presence of $NH_4OH$(5M), $CUSO_4$ (0.6 mg/ml) and $H_2O_2$ (3% vol/vol); 4) in the presence of NaOH (1M); 5) in the presence of NaOH(1M) and $CuSO_4$ (0.6 mg/ml); 6) in the presence of NaOH(1M), $CUSO_4$ (0.6 mg/ml) and $H_2O_2$ (3%). The mixture was stirred vigorously in air for 24 hours. Two volumes of ethanol were added, the precipitate is collected by centrifugation, and lyophilized to dryness. The resultant red melanin powder was dissolved in Avon Body Lotion at a concentration of 5% (wt/wt; melanin/lotion) and applied to the skin and hair of a volunteer. Excess material was removed by washing with soap and water, and both the amount as well as the color of the adhering melanin was assessed visually. A red or golden-red tan was achieved which did not rub off with application of water and soap to the skin.

Instead of using 10% wt/vol of aloin alone in water, the starting materials used may include 6.7% wt/vol dihydroxyphenylalanine+3.3% wt/vol aloin. In this embodiment a brown cosmetic melanin is produced.

Instead of using 10% wt/vol of aloin alone in water, the starting materials used may include 10% 3-dimethylamino phenol alone or 6.7% wt/vol 3-dimethylamino phenol+3.3% wt/vol co-monomer. In this embodiment a yellow cosmetic melanin is produced.

6.3. EXAMPLE 3: INDUSTRIAL PRODUCTION OF A COSMETIC MELANIN

Ingredients for the production of 100 kg (based on 100% yield) of a red cosmetic melanin are listed as follows:

| | |
|---|---|
| aloin | 100 kg |
| NH$_4$OH (concentrated) | 350 liters |
| CuSO$_4$ | 750 g |
| H$_2$O | 550 liters |
| H$_2$O$_2$ | 100 liters (incrementally) |

The ingredients are added in the order listed in a suitable mixing chamber. The mixture is aerated vigorously for 24 hours. The resultant melanin polymer is precipitated by the addition of ethanol (2.5 volumes, approximately 2500 liters). The precipitate is collected and dried in air. The melanin is then dissolved in Avon Body Lotion (described above in Section 5.3.3) at a concentration of 1% (wt/wt; melanin/lotion), and packaged for use as a cosmetic melanin.

Instead of using 100 kgs of aloin as starting material, 67 kg of dihydroxyphenylalanine+33 kg of aloin is used to produce a cosmetic melanin that is brown in color.

6.4. EXAMPLE 4: APPLICATION OF COSMETIC MELANIN TO THE SKIN AND/OR HAIR a) A red cosmetic melanin consisting of polymerized monomers of aloin (3 parts) is mixed in Avon Body Lotion (1% wt/wt; melanin/lotion), and applied manually to the skin and/or hair of an individual desiring a natural-appearing red or golden-red coloration. Excess material is removed by washing with soap and water. The melanin is substantive to the skin, i.e., it adheres to the skin. Once the excess melanin is washed off, the melanin that adheres to the skin does not wash off with water and soap or rub off with a towel or clothing and will not run off when immersed in water or swimming or during normal physical activity or due to sweating.

b) A red cosmetic melanin consisting of co-polymerized monomers of aloin (4 parts), 3-dimethylamino phenol (1 part) and linoleic acid (1 part) is mixed with Avon Body Lotion (5% wt/wt; melanin/lotion), and applied manually to the skin and/or hair of an individual desiring a natural-appearing red or golden-red coloration. Excess material is removed by washing with soap and water. The melanin is substantive to the skin, i.e., it adheres to the skin. Once the excess melanin is washed off, the melanin that adheres to the skin does not wash off with water and soap or rub off with a towel or clothing and will not run off when immersed in water or swimming or during normal physical activity or due to sweating.

c) A blue/green cosmetic melanin consisting of monomers of dihydroxynaphthalenesulfonic acid (2 parts) and aloin (1 part) is mixed in Avon Body Lotion, and applied manually to the skin of an individual desiring this hue. A blue/green hue can be used to soften the appearance of blemishes. Excess material is removed by washing with soap and water. The melanin is substantive to the skin, i.e., it adheres to the skin. Once the excess melanin is washed off, the melanin that adheres to the skin does not wash off with water and soap or rub off with a towel or clothing and will not run off when immersed in water or swimming or during normal physical activity or due to sweating.

6.5. EXAMPLE 5: CUSTOMIZED COSMETIC MELANINS

Powdered forms of a brown melanin, a red melanin, a purple melanin and a blue/green melanin, prepared according to the procedures described above in Section 5.3.3, are separately dissolved in Avon Body Lotion at a concentration of 1% (wt/wt; melanin/lotion). The melanin-containing lotions are then mixed with one another in a variety of proportions (e.g., 1:1:1; 1:2:1; etc.) and applied to the skin and/or hair of a volunteer. When the desired hue is achieved, e.g., the color that most approximates that of the hair and eye color of the volunteer, the mixed proportions are recorded, and the melanin "blend" has, thus, been customized to the individual.

6.6. EXAMPLE 6: USE OF COSMETIC MELANIN AS A PROTECTANT FROM UV RADIATION

A cosmetic melanin consisting of polymerized monomers of aloin (5 parts) and linoleic acid (1 part) is mixed with Avon Body Lotion (1% wt/wt; melanin/lotion) and applied to the skin of an individual. The inherent ultraviolet light absorbance of the melanin as well as its free radical scavenging characteristics provide protection from solar radiation to the individual's skin in the region wherein the melanin is applied.

The instant specification and claims are set forth by way of illustration and not limitation, and various modifications and changes may be made without departing from the spirit and scope of the present invention. The present invention is not to be limited in scope by the specific embodiments described which are intended as illustrations of individual aspects of the invention, and functionally equivalent methods and components are within the scope of the invention, in addition to those shown and described herein will become apparent to those skilled in the art from the foregoing description and accompanying drawings. Such modifications are intended to fall within the scope of the appended claims.

What is claimed is:

1. A melanin polymer consisting of monomeric units selected from the group consisting of 3-aminotyrosine, 3,4-dihydroxybenzoic acid, 3-amino,4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol and p-aminobenzoic acid, and further consisting of a co-monomer, which is an agent that enhances substantivity of the melanin polymer to human skin, said co-monomer being co-polymerized with the monomeric units, said melanin polymer characterized by being substantive to human skin and hair and being soluble in an aqueous cosmetic buffer at physiological pH and temperature.

2. The melanin polymer according to claim 1, wherein the co-monomer is an aromatic glycoside.

3. The melanin polymer according to claim 1, wherein the monomeric unit is dihydroxyphenylalanine and the co-monomer is aloin.

4. The melanin polymer according to claim 1, wherein the co-monomer is emodin.

5. The melanin polymer according to claim 1, wherein the co-monomer is alizarin.

6. The melanin polymer according to claim 1, wherein the co-monomer is a steroid.

7. The melanin polymer according to claim 1, wherein the co-monomer is cholesterol.

8. The melanin polymer according to claim 1, wherein the co-monomer is a carbazole alkaloid.

9. The melanin polymer according to claim 1, wherein the co-monomer is dihydroxycarbazole.

10. The melanin polymer according to claim 1, wherein the co-monomer is a fatty acid.

11. The melanin polymer according to claim 1, wherein the co-monomer is 9,10-dihydroxystearic acid.

12. The melanin polymer according to claim 1, wherein the co-monomer is linoleic acid.

13. The melanin polymer according to claim 1, wherein the co-monomer is linolenic acid.

14. The melanin polymer according to claim 1, comprising monomeric units of tyrosine.

15. The melanin polymer according to claim 1, comprising monomeric units of dihydroxyphenylalanine.

16. The melanin polymer according to claim 1, comprising monomeric units of 3-amino-tyrosine.

17. The melanin polymer according to claim 1, comprising monomeric units of 3-nitro-tyrosine.

18. The melanin polymer according to claim 1, comprising monomeric units of 3,4-dihydroxybenzoic acid.

19. The melanin polymer according to claim 1, comprising monomeric units of 3-amino-4-hydroxybenzoic acid.

20. The melanin polymer according to claim 1, comprising monomeric units of 3-dimethylamino phenol.

21. The melanin polymer according to claim 1, comprising monomeric units of p-aminobenzoic acid.

22. The melanin polymer according to claim 1, comprising monomeric units of 4,5-dihydroxynaphthalene-2-sulfonic acid.

23. The melanin polymer according to claim 1, comprising monomeric units of aloin.

24. A melanin polymer according to claim 1, comprising monomeric units of emodin.

25. A melanin polymer according to claim 1, comprising monomeric units of alizarin.

26. The melanin polymer according to claim 1, comprising a mixture of the monomeric units alizarin and dihydroxyphenylalanine.

27. A melanin polymer comprising monomeric units of dihydroxyindole-2-carboxylic acid co-polymerized with a co-monomer selected from the group consisting of aloin, emodin, and alizarin, said melanin polymer characterized by being substantive to human skin and hair and being soluble in aqueous cosmetic buffers at physiological pH and temperature.

28. A melanin polymer comprising monomeric units of 5,6-dihydroxyindole co-polymerized with a co-monomer selected from the group consisting of aloin, emodin, and alizarin, said melanin polymer characterized by being substantive to human skin and hair and being soluble in aqueous cosmetic buffers at physiological pH and temperature.

29. A method of obtaining a melanin polymer which comprises mixing a monomeric material selected from the group consisting of 3-aminotyrosine, 3,4-dihydroxybenzoic acid, 3-amino,4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol and p-aminobenzoic acid with a co-monomer selected from the group consisting of 9,10-dihydroxystearic acid, cholesterol, dihydroxycarbazole, aloin, emodin, alizarin, linoleic acid and linolenic acid and polymerizing the mixture in aqueous solution by oxidation in the presence of air:

(a) in the presence of a weak base; or (b) in the presence of a weak base and a salt of $Cu^{++}$ or $Fe^{++}$; or (c) in the presence of a weak base, a salt of $Cu^{++}$ or $Fe^{++}$ and an oxidant; or (d) in the presence of a strong base; or (e) in the presence of a strong base and a salt of $Cu^{++}$ or $Fe^{++}$; or (f) in the presence of a strong base, a salt of $Cu^{++}$ or $Fe^{++}$ and an oxidant;

and thereafter adding to the resulting solution of formed melanin polymer an alkanol, thereby to precipitate the melanin polymer from said solution.

30. The method according to claim 29, wherein the alkanol comprises ethanol.

31. A method of producing a naturally appearing tan on mammalian skin comprising applying to the skin a tan-producing effective amount of a melanin polymer consisting of monomeric units selected from the group consisting of 3-aminotyrosine, 3,4-dihydroxybenzoic acid, 3-amino,4-hydroxybenzoic acid, aloin, emodin, alizarin, tyrosine, dihydroxyphenylalanine, 4,5-dihydroxynaphthalene-2-sulfonic acid, 3-nitrotyrosine, 3-dimethylamino phenol and p-aminobenzoic acid, and further consisting of a co-monomer which is an agent that enhances substantivity of the melanin polymer to human skin, said co-monomer being co-polymerized with the monomeric units, said melanin polymer characterized by being substantive to human skin and hair and being soluble in an aqueous cosmetic buffer at physiological pH and temperature.

* * * * *